United States Patent [19]

Levesque

[11] 4,226,237

[45] Oct. 7, 1980

[54] LAYERED ABSORBENT STRUCTURE

[75] Inventor: Yvon G. Levesque, Montreal, Canada

[73] Assignee: Johnson & Johnson, New Brunswick, N.J.

[21] Appl. No.: 7,279

[22] Filed: Jan. 30, 1979

[51] Int. Cl.³ .................. A61F 13/20; A61F 13/16
[52] U.S. Cl. .............................. 128/285; 128/287; 128/290 R; 128/DIG. 30
[58] Field of Search .............. 128/284, 285, 287, 290, 128/296, 156; 162/92, 129; 428/248, 282, 287, 326

[56] References Cited

U.S. PATENT DOCUMENTS

| | | | |
|---|---|---|---|
| 610,957 | 9/1898 | Zschorner | 162/92 |
| 642,387 | 1/1900 | Tempied et al. | 128/156 |
| 1,328,267 | 1/1920 | Cowan | 162/92 |
| 4,047,531 | 9/1977 | Karami | 128/287 |
| 4,102,340 | 7/1978 | Mesek et al. | 128/287 |
| 4,105,033 | 8/1978 | Chatterjee et al. | 128/285 |

Primary Examiner—C. Fred Rosenbaum
Attorney, Agent, or Firm—Jason Lipow

[57] ABSTRACT

A product is provided for absorbing body fluid that has the property of retaining a greater proportion of absorbent fluid in an interior layer. The product includes an absorbent element having a plurality of absorbent layers including a first layer comprising of cellulose fibers. Adjacent to the first layer is a second layer comprising, in admixture, peat moss and finely ground mechanical wood pulp, the mechanical wood pulp being present in a ratio of at least 0.35 grams per gram of peat moss.

13 Claims, 10 Drawing Figures

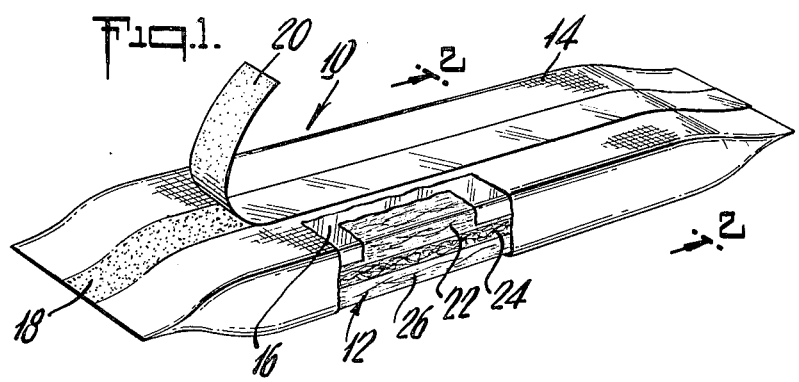
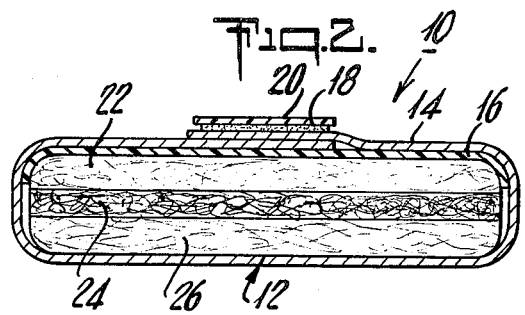
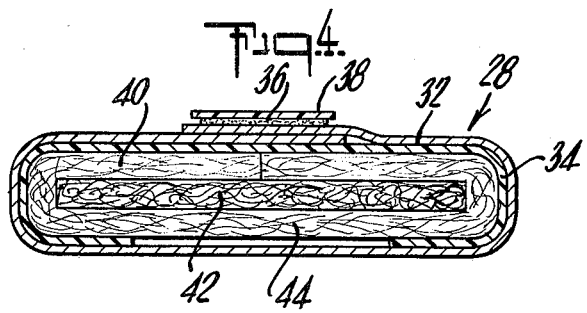
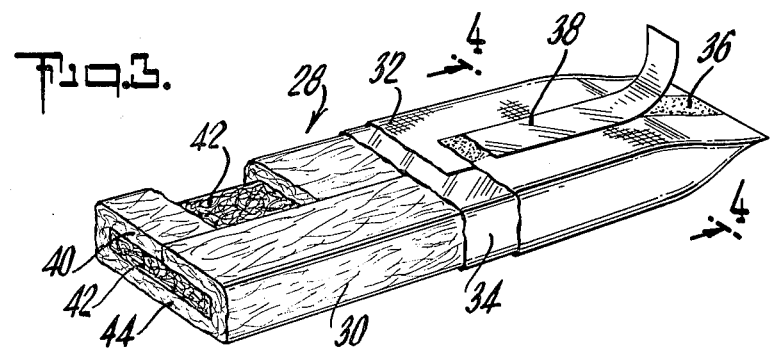

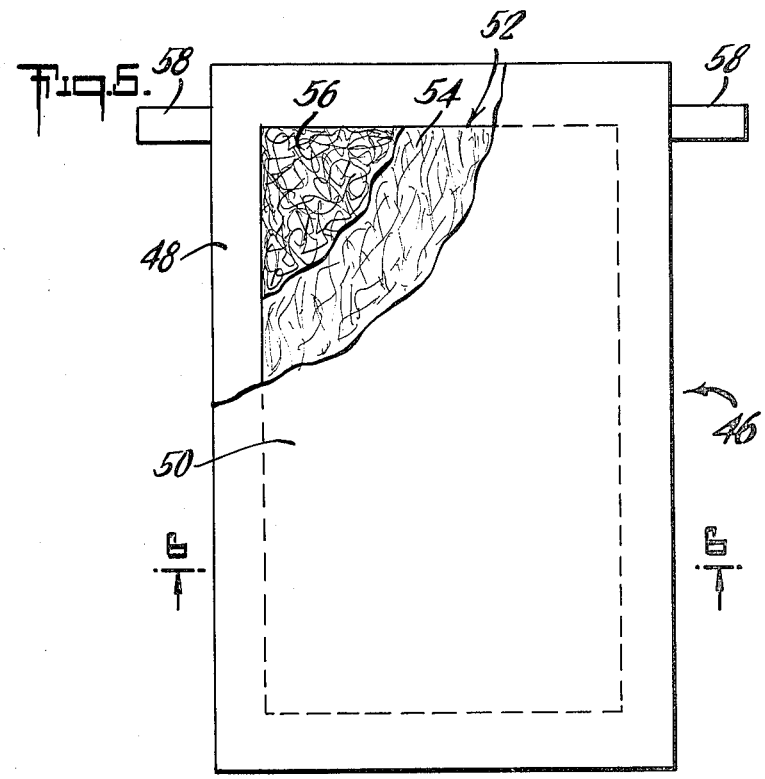
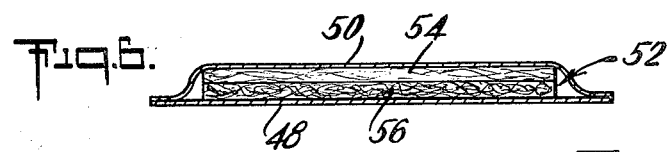
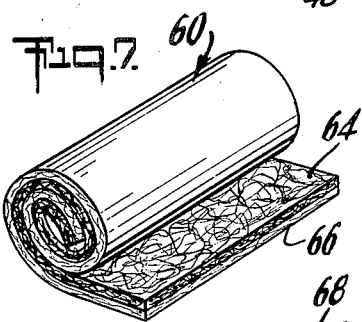
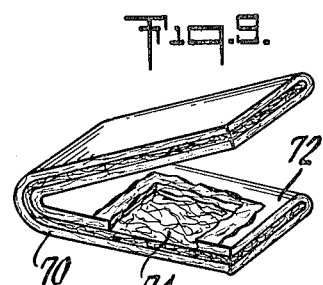
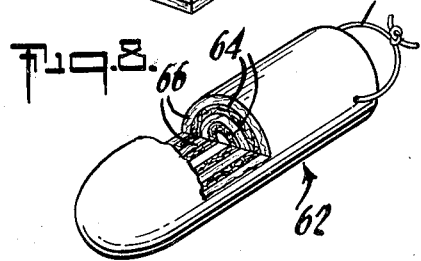
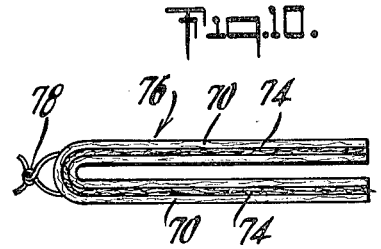

LAYERED ABSORBENT STRUCTURE

BACKGROUND OF THE INVENTION

This invention relates to absorbent products and particularly to such products which are to be worn by a user against the body and are designed to absorb body exudates, e.g., diapers, sanitary napkins, catamenial tampons and the like.

These products generally comprise an absorbent element such as a pad or core of absorbent material, optionally enveloped by a cover which is pervious to body exudate at least on the side in contact with the body. Frequently, as is the case with disposable diapers and some sanitary napkins, the side worn away from the body is provided with a barrier sheet, i.e., a sheet of material impervious to body fluid, to protect the garments of the wearer. This barrier sheet may form a part of the cover enveloping the absorbent material or may underlie such a cover on the side away from the body.

In the main, such products have performed their primary function, i.e., they have absorbed and retained body fluid. A major drawback associated with such products, however, is that after the user has worn them for a period of time, the products may fail before they become fully saturated by having fluid strike through onto an external surface contacting the user's garment or by having the surface worn against the body become so wet with fluid that the resulting discomfort causes the user to discard the product. Accordingly, there is a need for an absorbent product which makes full use of the absorbent material provided and keeps absorbed fluid away from the external surfaces of the product.

One attempt to solve this problem is described in U.S. Pat. No. 3,017,304 and 3,612,055 wherein a skin is provided on the side of the product worn away from the body and is designed to draw liquid away from the body facing side. Unfortunately, this skin has little fluid retention capacity per se and soon becomes saturated and ineffective. In U.S. Pat. No. 4,047,531 a layered structure comprising juxtapositioned layers of relatively hydrophobic and hydrophilic wood pulp are used in an effort to solve the problem. Unfortunately, the use of relatively hydrophobic material tends to decrease the overall capacity of the absorbent product and hence does not represent a satisfactory solution. The need for an absorbent product capable of absorbing as much fluid or more than conventional products but which will keep absorbed fluid away from the external surfaces of the product has, heretofore, gone unsatisfied.

SUMMARY OF THE INVENTION

In accordance with this invention, a product is provided for absorbing body fluid that is at least as absorbent as conventional products and also has the property of retaining a greater proportion of the absorbed fluid in an interior layer rather than allowing this fluid to be retained at or near the surface of the product. Specifically, the invention is directed toward an improvement in an absorbent product having an absorbent element which includes a plurality of absorbent layers and includes at least a first layer of cellulose fibers. Adjacent to the first layer is a second layer which comprises, in admixture, peat moss and finely ground mechanical wood pulp in a weight ratio of at least about 0.35 grams of said wood pulp per gram of peat moss. Preferably there is at least 0.4 grams of said finely ground wood pulp per gram of peat moss. Such finely ground mechanical wood pulp may be selected from such materials as groundwood pulp, refiner wood pulp or, thermomechanical wood pulp. The particle size of the mechanical wood pulp can be characterized by the Canadian Standard Freeness (hereinafter CSF, measured by TAPPI Test Method T-227). Preferably the mechanical wood pulp will have a CSF value of from 30–600, and more preferably from 60–300. The second layer may also comprise longer fibered absorbent materials such as chemical wood pulp and/or rayon. Preferably, the peat moss is bleached to a lightness of at least about 70, as measured on the Hunter Colour Scale System "C". This second layer has the property of retaining at least about twice the weight of absorbed fluid as the first layer, prior to product failure.

It is preferred that the absorbent structure defined herein include at least a third layer of cellulose fiber and that the second layer comprising the peat moss be sandwiched between the first and third layers thereby forming an interior layer of the absorbent structure. In this manner, because of the unique capacity of the defined structure to preferentially retain absorbed fluid in the second layer, fluid is kept away from the exterior of the absorbent element and hence away from the exterior surfaces. Surprisingly, this is accomplished by use of a material, peat moss, which does not have, per se, any greater fluid absorbing capacity than common wood pulp, is economical, and yet uniquely provides the desired result.

In one embodiment, the absorbent element of this invention is incorporated into a sanitary napkin which also includes a fluid pervious, non-woven cover and, optionally, an impervious, barrier sheet. The unique, preferential retention of the second layer, with respect to the first and third layers, keeps both the body-facing and the garment-facing surfaces relatively dry and adds to the comfort of the user and the life of the product.

In a second embodiment, the absorbent element is incorporated into a catamenial tampon wherein the unique construction of the element, resulting in the aforementioned preferential retention, allows the tampon to "fill from the center outwardly", thereby increasing the useful life of the tampon and reducing the tendency for failure by leakage around an externally saturated tampon.

In still another embodiment, the element is incorporated into a disposable diaper where once again the property of preferential retention keeps both the body facing and the garment facing surfaces of the product drier and increases the life of the product.

BRIEF DESCRIPTION OF THE DRAWINGS

Referring to the drawings:

FIG. 1 is a perspective view of a sanitary napkin incorporating therein the absorbent structure of this invention with parts removed therefrom in order to illustrate internal features;

FIG. 2 is a transverse cross-sectional view of the napkin of FIG. 1, taken through line 2—2;

FIG. 3 is a perspective view of a second embodiment of a sanitary napkin incorporating the structure of the invention with parts removed therefrom in order to illustrate internal features;

FIG. 4 is a transverse cross-sectional view of the napkin of FIG. 3 taken through line 4—4;

FIG. 5 is a planar view of a disposable diaper incorporating the structure of the invention with parts removed therefrom in order to illustrate internal features;

FIG. 6 is a transverse cross-sectional view of the diaper of FIG. 5 taken along line 6—6;

FIG. 7 is a perspective view of the structure of the invention, partially rolled into a tampon blank;

FIG. 8 is a perspective view of a tampon made from the blank of FIG. 7;

FIG. 9 is a perspective view of the structure of the invention, partially folded into a tampon blank; and FIG. 10 is a perspective view of a tampon made from the blank of FIG. 9.

DETAILED DESCRIPTION OF THE INVENTION

Referring to the drawings, FIGS. 1 and 2 illustrate in perspective and transverse cross-sectional views, respectively, a sanitary napkin incorporating as an absorbent element the structure of this invention. The napkin 10 comprises an absorbent element 12 enveloped by a fluid-pervious cover 14 which may be any woven or non-woven material pervious to body fluid striking its surface, such covers being well-known in the art. A fluid-impervious barrier sheet 16 is provided on the side of the napkin to be worn against the garment and away from the body and is sandwiched between the cover 14 and the element 12. The barrier sheet inhibits fluid from passing onto an undergarment and may be constructed of any thin, flexible, relatively body fluid impervious material, for example a polymeric film such as polyethylene, polypropylene, cellophane or a usually fluid-pervious material that has been treated to be impervious such as impregnated fluid-repellant paper. The illustrated napkin is of a kind to be positioned in the undergarment of the user by adhesive means. To that end, the side facing the undergarment is provided with a longitudinally extending element of pressure-sensitive adhesive 18. A protective strip 20 is provided, overlying the adhesive element 18, to protect the adhesive element prior to use.

In accordance with the teachings of this invention, the absorbent element 12 is made up of a plurality of absorbent layers. A first layer 22 comprises cellulosic fibers and may, for example, comprise loosely associated fibers of wood pulp, regenerated cellulose, cotton fibers, or such chemically or physically modified cellulose fibers as alkyl-carboxylated cellulose, grafted cellulose or the like. Alternatively, the first layer may take the form of a more ordered cellulose fiber configuration such as wadded tissue paper or other bonded structures. Adjacent to this first layer 22, and in face-to-face relationship therewith, is a second layer 24 which is described in my co-pending application, Ser. No. 7280, filed together herewith which was, in turn, a continuation-in-part of my co-pending application Ser. No. 879,832 filed on Feb. 21, 1978. This second layer 24 comprises, in admixture, peat moss and finely ground mechanical wood pulp in a weight ratio of at least about 0.35 grams of said mechanical wood pulp per gram of peat moss. Preferably there is at least 0.4 grams of said finely ground mechanical wood pulp per gram of peat moss. Such finely ground mechanical wood pulp may be selected from such materials as groundwood pulp, refiner wood pulp or, thermomechanical wood pulp. Groundwood pulp is essentially trees and branches which have been debarked, cleaned and then ground into particle matter. Refiner wood pulp differs from groundwood pulp only in that the grinding step utilizes a refiner, i.e., a disk-like device well known in the art and generally having metallic ribs at the peripheral sections thereof which last contact the wood particles and help to separate the wood fibers without excessively damaging them. Thermomechanical wood pulp is similar to refiner pulp with the exception that the wood particles are heated when in the refiner, usually with steam, and this heating further aids in separating the wood fibers. The common characteristic of these mechanical pulps is that no attempt has been made to separate the fibers by chemical means although they may later, after being reduced to fine particulate matter, be subjected to chemical treatment, e.g., bleaching.

The particle size of the mechanical wood pulp can be characterized by the Canadian Standard Freeness (hereinafter CSF, measured by TAPPI Test Method T-227). Preferably the mechanical wood pulp will have a CSF value of from 30–600, and more preferably from 60–300. The second layer may also comprise longer fibered absorbent materials such as chemical wood pulp and/or rayon. Preferably, the peat moss is bleached to a lightness of at least about 70, as measured on the Hunter Colour Scale System "C".

Preferably, the peat moss is uniformly distributed in the second layer and has been bleached or otherwise processed to attain the specified colour level. Peat moss having this colour level may be readily obtained by treatment in accordance with the process for bleaching peat moss as has been described in co-pending application Ser. No. 879,833 which is incorporated herein by reference. The starting peat moss of this process is of the sphagnum type and will hold at least about 15 and preferably about 20 times its weight of water. The peat moss is screened between 10 and 100 mesh screens, and the material that stays on a 10 mesh screen, primarily roots and branches, is discarded. Also, the material that passes through the 100 mesh screen; namely, the fines, which add little to the absorbent properties and are very difficult to bleach, are also discarded. Hence, the starting peat moss is from about 0.15 millimeters (100 mesh) to 1.8 millimeters (10 mesh). The peat moss is bleached by treatment with both chlorine and calcium in the form of limestone. The bleaching may be carried out as a batch operation; that is, the peat moss is diluted with water to a concentration of about 2% by weight, treated with chlorine, followed by a calcium carbonate treatment by acid washes and water washed to provide the desired degree of whiteness.

Preferably, the finely ground mechanical wood pulp component of the second layer and, optionally, the long fibered absorbent material such as rayon and/or chemical pulp (e.g., kraft or sulfate pulp) are added to the still wet, bleached peat and the mixture is slurried and formed into board. The board is then dried and ground to form the absorbent second layer.

The components of this second layer may be in loosely associated form as is obtained by means well known in the art for forming absorbent pads. It has been discovered in accordance with my aforementioned application that the presence of the finely ground mechanical wood pulp will give this second layer substantial integrity. Additionally, the components may be stabilized by use of adhesive binders so that the layer has still greater structural integrity. As shown in the illustrated embodiment, a third layer 26 is provided consisting of the same material as the first layer.

The napkin of FIGS. 1 and 2, incorporating the teachings of this invention, has been discovered to have the surprising property of preferential retention before it becomes fully saturated. Said in other words, it has been discovered that body fluid striking the body-facing surface of the napkin neither remains at this surface nor becomes distributed evenly throughout the absorbent element 12. Instead, a disproportionate quantity of body fluid is retained in the second layer of the structure. Preferably, this layer 24 retains at least about twice the weight of absorbed fluid as any of the other layers, i.e., layer 22 or layer 26. More, preferably, this layer retains at least 2.5 times as much. This result is obtained irrespective of whether or not the relative weight of the second layer of this invention is greater than or equal to the weight of the first layer. This is particularly surprising in that when, for example, a layer of wood pulp is used as the first layer and a layer comprising, by weight, thirty percent bleached, sphagnum peat moss, thirty eight percent groundwood, eight percent kraft wood pulp and 24% rayon fiber, the saturated water retention of each of these layers, when measured alone, is essentially the same. Notwithstanding this, the preferential retention is realized.

While preferential retention will be manifested throughout a large variance in the relative weights of the first and second layers of the structure of the invention, it is preferred that the first layer weight from about 0.1 to about 2.0 times the weight of the second layer and preferably from about 0.5 to about 1.0 times such weight. If this ratio is too small, the protective effect of the first layer will be disadvantageously reduced. On the other hand, if this ratio is too large, the effect of preferential retention will be minimized to the point of insignificance, as the second layer will soon be saturated.

Referring now to FIGS. 3 and 4, illustrated therein is another form of sanitary napkin 28 incorporating the structure of this invention. As in the prior described embodiment, the napkin 28 includes an absorbent element 30 enveloped by a fluid pervious woven or non-woven cover 32. Sandwiched between the cover 23 and the element 30 is a fluid impervious barrier sheet 34 for protecting the garments of the user. The barrier sheet 34 overlies the garment facing major surface of the absorbent element 30 as well as the sides and the extreme longitudinal portions of the body facing major surface of the element 30. The illustrated napkin 28 is intended for adhesive attachment to the crotch portion of the wearer's undergarment and hence is provided, on the garment facing major surface, with a pressure sensitive adhesive element 36 protected by a peelable protective strip 38.

As in the prior embodiment, the absorbent element is made up of first, second and third layers 40, 42, 44 in face-to-face relationship. In this instant napkin 28 however, the first and third layers 40, 44 are formed from a generally rectangular sheet of bonded wood pulp fibers folded into the form of a C by folding the portions adjacent to each longitudinal edge toward each other so that they abut and overlie the central portion of the sheet. The second layer in this embodiment comprises a mixture of peat moss and ground mechanical wood pulp in the proportions set out in connection with the first described embodiment, these components being bonded together to form a dimensionally stable second layer 42. This second layer is sandwiched between the first and third layers 40 and 44, respectively. Again, this construction exhibits the preferential retention described herein.

Referring to FIGS. 5 and 6 of the drawings, there is shown a disposable diaper 46 incorporating the structure of the invention. The diaper comprises an impervious backing sheet 48 which again is preferably a film and a pervious facing sheet 50 which may be a nonwoven fabric, a spun bonded fabric, a pervious film material or the like. In the illustrated embodiment, the facing and backing are co-extensive and are sealed together at their margins. Positioned between the facing and the backing is an absorbent element 52 of the instant invention. The absorbent element 52 is smaller than the facing and backing and is positioned inwardly from the edges thereof. The absorbent element comprises a first layer 54 placed adjacent the facing 50 and containing long fiber wood pulp. A second layer 56 is provided which contains peat moss and ground mechanical wood pulp in accordance with this invention and meets the conditions set out in connection with the second layer of FIG. 1. The opposed latteral edges of the diaper are provided with adhesive tape tabs 58 for securing the diaper about the wearer. In use, this construction exhibits the preferential retention property described herein and tends to keep absorbent liquid away from the facing layer.

Referring now to FIGS. 7 and 8 illustrated therein, respectively, is a tampon blank 60 and a finished tampon 62 incorporating this present invention. The tampon blank is provided with a generally rectangular first layer 66 of the structure of the invention consisting of a pad of wood pulp fibers. Overlying this first layer 66 is a second layer 64 consisting of the peat moss and ground mechanical wood pulp mixture described herein. The blank is formed into a cylinder by rolling from one end to the other in a direction parallel to the longitudinal sides of the composite layers. The rolled blank thereby exhibits alternating strata of first and second layer materials in radial cross-sections. This blank is then compressed in a die to the desired tampon 62 shape, as illustrated in FIG. 8. The tampon 62 is provided with the usual withdrawal string 68 which may be sewn through the removal end of the tampon or applied by other means known in the art, such as being looped or tied around the rectangular structure of the invention prior to rolling.

FIGS. 9 and 10 illustrate still another embodiment of this invention in a catamenial tampon. A rectangular pad 70 of wood pulp is laid upon a porous non-woven cellulosic fabric cover 72 and constitutes the first and third layers of the structure of this invention. Overlying this pad 70 is a layer 74 of the peat moss and ground mechanical wood pulp absorbent mixture which constitutes the second layer of this invention. The pad 70 with the non-woven cover 72 is then folded about its longitudinal center and folded once more into a U-shaped blank, as illustrated in FIG. 9. The blank is then placed in a cylindrical die and compressed radially and/or longitudinally into the desired tampon shape 76 as shown in FIG. 10. A withdrawal string 78 is provided at the withdrawal end of the compressed tampon 76 and may be attached in a manner similar to that described above, i.e., sewn on, looped or tied around the pad 70 prior to folding, etc. The finished tampon 76 will then comprise centrally located strata or layers of peat moss containing absorbent material juxtapositioned against layers of wood pulp. In use, because of the preferential retention properties of this structure, the outer layer 70 will retain disproportionately less fluid than the inner layers 74 and hence tend to become saturated last. Said in other words the tampon will fill from the inside out. Accordingly, fluid striking the outside surface of the tampon will always strike unsaturated absorbent material and thereby will be less likely to leak past the tampon. To illustrate the advantages of the invention, the following examples are given. Unless otherwise stated, all percentages are by weight. In each of these examples the absorbent has been treated so as to include a wetting agent in quantities of less than 0.5% by weight of dry absorbent. The wetting agent used is a sodium dioctyl sulfo succinate containing agent manufactured by the Rohm & Haas Company and sold by them under the tradename Triton GR-5.

EXAMPLE 1

A series of samples are prepared in accordance with the teachings of this invention. Each of the samples consists of a plurality of rectangular absorbent layers measuring 9 inches by 12 inches.

The first sample consists of a first and second layer, the first layer weighing 18.5 grams and made up of 90% long fiber Kraft wood pulp and 10% rayon fibers. This mixture is stabilized with an acrylic latex emulsion adhesive binder and contains 5.7% of said binder based on the weight of the binder free fibers. The second layer weighs 15.5 grams and consists of 35.0% bleached peat moss having a colour intensity of 70 as measured on the Hunter Colour Scale System "C", 43.5% groundwood pulp having a CSF value of 80, 8.5% of long fiber Kraft wood pulp, and 13.0% of rayon fibers having a denier of 1.5 and a staple length of 1.2 inches. This mixture is bonded with the same adhesive and in the same amounts as is the first layer.

The second sample consists of first and second layers, wherein the second layer weights 9 grams and is otherwise identical to that described above in connection with the first sample. The first layer is made up of 9.0 grams of air laid Kraft wood pulp.

The third sample consists of three layers wherein the first layer is made up of 12.5 grams of air laid Kraft wood pulp, the second layer of 14.5 grams of the same peat moss containing material described in connection with the first sample, and the third layer consists of a single ply of 2.5 grams of paper wadding.

These samples are tested as follows to determine their preferential liquid retention capacity. Each sample is placed upon a flat surface, with the first layer facing up, and thirty cubic centimeters of a 1%, by weight, NaCl solution are deposited at the center of the first layer of each sample. The liquid is allowed to diffuse through the sample for a period of twenty minutes. Thereafter, a 7.5 cm diameter disc is punched out of the center of the sample at the point of liquid deposition and the fluid retained per unit weight of each layer of each sample is measured. The results are shown in Table I below.

TABLE I

| Sample | Layer Description | Fluid Distribution (cc/gm) |
|---|---|---|
| 1 | First Layer: Kraft (Bonded) | 2.0 |
|   | Second Layer: Peat | 4.8 |
| 2 | First Layer: Kraft (Fluff) | 2.5 |
|   | Second Layer: Peat | 5.55 |
| 3 | First Layer: Kraft (Fluff) | 1.45 |

TABLE I-continued

| Sample | Layer Description | Fluid Distribution (cc/gm) |
|---|---|---|
|   | Second Layer: Peat | 4.55 |
|   | Third Layer: Tissue | 1.25 |

As the Table I indicates, the juxtapositioning of the layers of the samples made in accordance with the teachings herein produces the unique preferential fluid distribution of this invention. Specifically, from 2.2 to 3.13 times as much fluid is retained in the peat layer than the next most retentive layer.

EXAMPLE 2

A series of sanitary napkins are prepared having the construction shown in FIGS. 1 and 2. Specifically, the napkins have an overall length and width of 9.72 inches and 2.38 inches, respectively. They are provided with a non-woven cover of bonded, 100% rayon fibers weighing 17.0 gm/sq. yard. For ease of construction, the samples are provided with a single ply of tissue which overwraps the 0.5 mil. polyethylene barrier sheet provided and underlies the nonwoven cover. Each of the napkins is provided with an absorbent element comprising a plurality of layers and in each of the samples, the top (closest to the body contacting side) and bottom (closest to the garment contacting side) layers of the element both are 4 gram layers of air laid, fluffed, bleached, Kraft wood pulp comprising by weight 90% softwood pulp and 10% hardwood pulp. The middle layer of the absorbent element consist of the following materials for each sample, with the peat moss and groundwood pulp being the same as that described in connection with Example 1.

Control Samples: A layer of high bulk wadding consisting of three plies of creped tissue folded four times to produce a total of twelve plies weighing 1.55 gms.

Samples A and B: A second (from the top) layer of high bulk wadding identical to that of the second layer of the control samples and a third layer consisting of 35.0% peat moss, 43.5% groundwood pulp; 8.5% long fibered Kraft wood pulp and 13.1% rayon fiber.

Sample C: A middle layer consisting of a laminate construction having a top stratum of wood pulp, a central stratum of a mixture of 40% peat moss, 50% groundwood and 10% Kraft pulp, and a bottom stratum of wood pulp; the laminate weighting 4 grams and being bonded throughout with 5% of adhesive per gram of adhesive free material.

Sample D: A middle layer consisting of 1.55 grams of a mixture, by weight of, 40% peat moss, 50% groundwood and 10% Kraft wood pulp; the layer being bonded with about 4%, by weight, of adhesive.

Sample E: A middle layer consisting of a laminate, having a top stratum with a composition identical to that of the middle layer of Sample D and a bottom stratum composed of wood pulp. Both stratum are bonded with about 4% by weight of adhesive and each weight 1.2 grams.

The samples are all tested by introducing onto the top of the napkins ersatz menstrual fluid at a rate of 3.1 cc/hr. for two hours and thereby providing a total liquid intake of 6.2 cc. The samples are then reweighted to determine the fluid retention distribution and these results are reported in Table II below:

TABLE II

| Sample | Top Layer Description | Top Layer Weight (GM) | Top Layer % Fluid Absorbed | Second Layer Description | Second Layer Weight (GM) | Second Layer % Fluid Absorbed | Third Layer Description | Third Layer Weight (GM) | Third Layer % Fluid Absorbed | Bottom Layer Description | Bottom Layer Weight (GM) | Bottom Layer % Fluid Absorbed |
|---|---|---|---|---|---|---|---|---|---|---|---|---|
| Control 1 | Wood Pulp | 4 | 27 | Wadding | 1.55 | 32 | None | | | Wood Pulp | 4 | 18 |
| Control 2 | Wood Pulp | 4 | 17 | Wadding | 1.55 | 34 | None | | | Wood Pulp | 4 | 21 |
| A | Wood Pulp | 4 | 17 | Wadding | 1.55 | 10 | Unbleached Peat Pulp | 2.67 | 54 | Wood Pulp | 4 | 0 |
| B | Wood Pulp | 4 | 17 | Wadding | 1.55 | 6 | Bleached Peat Pulp | 2.67 | 56 | Wood Pulp | 4 | 0 |
| C | Wood Pulp | 4 | 13 | None | | | Sandwiched Peat Pulp | 4 | 75 | Wood Pulp | 4 | 0 |
| D | Wood Pulp | 4 | 23 | None | | | Foam Bonded Peat Pulp | 1.55 | 65 | Wood Pulp | 4 | 2.0 |
| E | Wood Pulp | 4 | 25 | None | | | Peat Pulp Laminate | 2.4 | 55 | Wood Pulp | 4 | 3.0 |

As can be seen from the results, the middle layer of the control samples retained no more than 1.6 and 1.7 times the quantity of fluid than the next most retentive layer. In contrast thereto, the peat moss containing layer of samples made in accordance with the teachings of this invention retained from 2.2 to 5.8 times as much fluid as the next most retentive layer. Also, in contrast to the control samples, the next most retentive layer was the top layer. The bottom layer of the samples made in accordance with the invention was found to have retained at most only a very small percentage of the total absorbed fluid.

EXAMPLE 3

A series of samples of sanitary napkins are made having the general construction of the napkins illustrated in FIGS. 3 and 4. In each case the napkins have an overall length of 7.75 inches and a width of 2.25 inches. The porous cover is a 100% rayon non-woven fabric and a 0.5 mil. thick polyethylene film is used as the barrier sheet. The C-folded material consists of about 2.45 grams of 85% wood pulp and 15% rayon, bonded with 1.5% by weight of an adhesive. In the control samples, the absorbent layer inserted within the C-fold consists of three plies of 85% wood pulp and 15% rayon bonded with 1.5% adhesive and having a total weight of 3.7 grams. Samples made in accordance with this invention were provided with an insert layer consisting of, by weight, 35.2% peat moss, 44% ground wood pulp, 8.8% long fibered Kraft wood pulp and 12% rayon, bonded with 1.5%, by weight, adhesive. The samples were tested in vitro, using ersatz menstrual fluid and depositing such fluid at the rate of 3 cc/hr. for 3 hours and a total of 9 cc's per napkin. The napkins were then weighed to determine the distribution of the retained fluid in each layer, and the results are reported in the Table below.

TABLE III

| Sample | % Fluid In C-Fold | % Fluid In Insert |
|---|---|---|
| Control | 37.0 | 59 |
| Peat Moss Insect | 20.0 | 79 |

As can be seen, the central insert retained only 1.6 times as much fluid as the C-fold whereas the Sample made in accordance with this invention retained almost 4.0 times as much.

Samples of the above-described construction are tested, in vivo, by two menstruating subjects, user 1 and 2. Each user wore both the control and peat moss insert samples during the active part of her day. The napkins are returned and the distribution of menstrual fluid retained in each of the components is measured and reported in Table IV below.

TABLE IV

| Sample | User | Hrs. Worn | Total Fluid Absorbed (GM.) | % Retained In C-Fold | % Retained In Insert |
|---|---|---|---|---|---|
| Control | 1 | 4 | 3.95 | 46.8 | 52.7 |
|  | 2 | 2 | 4.45 | 49.4 | 44.3 |
| Peat Moss Insert | 1 | 5 | 4.65 | 18.1 | 71.4 |
|  | 2 | 2.5 | 5.87 | 17.5 | 76.4 |

What is claimed is:

1. A product for absorbing body fluids having an absorbent element consisting of a plurality of absorbent layers and including at least first and second adjacent absorbent layers; said first layer comprising cellulose fibers and said second layer comprising, in admixture, peat moss and finely divided ground mechanical wood pulp in a weight ratio of at least about 0.35 grams of said mechanical wood pulp per gram of said peat moss; said ground wood pulp having a Canadian Standard Freeness of from about 30 to about 600; whereof said second layer preferentially absorbs at least about twice the weight of absorbed fluid as said first layer.

2. The product of claim 1 wherein said peat moss is bleached peat moss having a lightness of at least about 70 as measured on the Hunter Colour Scale System "C".

3. The product of claim 1 wherein said second layer also comprises long fibered absorbent material.

4. The product of claim 3 wherein said long fibered absorbent material is chemical wood pulp.

5. The product of claim 3 wherein said long fibered absorbent material is rayon.

6. The product of claim 1 wherein said finely ground mechanical wood pulp is groundwood pulp.

7. The product of claim 1 wherein said finely ground mechanical wood pulp is refiner wood pulp.

8. The product of claim 1 wherein said finely ground mechanical wood pulp is thermomechanical wood pulp.

9. The product of claim 1 wherein said finely ground wood pulp has a Canadian Standard Freeness Value of from about 60–300.

10. The product of claim 1 wherein said plurality of absorbent layers includes at least a third absorbent layer and said second layer is sandwiched between said first and third layers.

11. A disposable diaper comprising an impervious backing sheet, a pervious facing sheet and an absorbent element smaller than said sheets and disposed therebetween, said absorbent element comprising a plurality of absorbent layers and including at least first and second adjacent absorbent layers; said first layer comprising cellulose fibers and said second layer comprising, in admixture, peat moss and finely divided ground mechanical wood pulp in a weight ratio of at least about 0.35 grams of said mechanical wood pulp per gram of said peat moss; said mechanical wood pulp having a Canadian Standard Freeness of from about 30 to about 600; whereof said second layer preferentially absorbs at least about twice the weight of absorbed fluid as said first layer.

12. A sanitary napkin comprising an absorbent element having cover enveloping said element, said absorbent element comprising a plurality of absorbent layers and including at least first and second adjacent absorbent layers; said first layer comprising cellulose fibers and said second layer comprising, in admixture, peat moss and finely divided ground mechanical wood pulp in a weight ratio of at least about 0.35 grams of said mechanical wood pulp per gram of said peat moss; said mechanical wood pulp having a Canadian Standard Freeness of from about 30 to about 600; wherein said second layer preferentially absorbs at least about twice the weight of absorbed fluid as said first layer.

13. A catamenial tampon comprising an absorbent element said absorbent element comprising a plurality of absorbent layers compressed together and including at least first and second adjacent absorbent layers; said first layer comprising cellulose fibers and said second layer comprising, in admixture, peat moss and finely divided ground mechanical wood pulp in a weight ratio of at least about 0.35 grams of said mechanical wood pulp per gram of said peat moss; said mechanical wood pulp having a Canadian Standard Freeness of from about 30 to about 600; wherein said second layer preferentially absorbs at least about twice the weight of absorbed fluid as said first layer.

* * * * *